(12) United States Patent
De Sanoit et al.

(10) Patent No.: US 9,121,107 B2
(45) Date of Patent: Sep. 1, 2015

(54) METHOD OF ACTIVATING A DOPED DIAMOND ELECTRODE

(75) Inventors: Jacques De Sanoit, Rungis (FR);
Raphael Kiran, Hannover (DE);
Emmanuel Scorsone,
Magny-les-Hameaux (FR)

(73) Assignee: Commissariat A L'Energie Atomique et aux 'energies alternatives, Paris (FR)

( * ) Notice: Subject to any disclaimer, the term of this patent is extended or adjusted under 35 U.S.C. 154(b) by 86 days.

(21) Appl. No.: 13/984,517

(22) PCT Filed: Feb. 16, 2012

(86) PCT No.: PCT/EP2012/052689
§ 371 (c)(1),
(2), (4) Date: Aug. 8, 2013

(87) PCT Pub. No.: WO2012/110600
PCT Pub. Date: Aug. 23, 2012

(65) Prior Publication Data
US 2013/0313120 A1 Nov. 28, 2013

(30) Foreign Application Priority Data
Feb. 18, 2011 (FR) ...................... 11 51341

(51) Int. Cl.
*C25B 11/12* (2006.01)
*C25D 11/00* (2006.01)
*G01N 27/38* (2006.01)

(52) U.S. Cl.
CPC ................ *C25D 11/00* (2013.01); *C25B 11/12* (2013.01); *G01N 27/38* (2013.01)

(58) Field of Classification Search
CPC ...................................................... C25B 11/12
See application file for complete search history.

(56) References Cited

FOREIGN PATENT DOCUMENTS

WO 2008148861 A1 12/2008

OTHER PUBLICATIONS

Becker, D., "The impedance of fast charge transfer reactions on boron doped diamond electrodes", Electrochimica Acta, Elsevier Science Publishers, Barking, GB, vol. 49, No. 1, pp. 29-39 (Dec. 30, 2003).
De Sanoit, J., "Electrochemical diamond sensors for TNT detection in water", Electrochimica Acta, Elsevier Science Publishers, Barking, GB, vol. 54, No. 24, pp. 5688-5693 (Oct. 1, 2009).
Deslouis, C., "Electrochemical behaviour of (111) B-Doped Polycrystalline Diamond: Morphology/surface conductivity/activity assessed by EIS and CS-AFM", Diamond and Related Materials, Elsevier Science Publishers, Amsterdam, NL, vol. 20, No. 1, pp. 1-10 (Jan. 1, 2011).

(Continued)

Primary Examiner — Harry D Wilkins, III
Assistant Examiner — Ho-Sung Chung
(74) Attorney, Agent, or Firm — Nixon Peabody, LLC

(57) ABSTRACT

A method for electrochemically activating a doped diamond electrode by bringing the electrode into contact with an aqueous solution containing an electrolyte and applying at least one electrical pulse to the electrode. This method may be used to restore the electrochemical reactivity of a doped diamond-based electrode, the activation of the electrode in some cases possibly being done in the same aqueous solution containing an electrolyte in which the electrode lost its electrochemical reactivity.

13 Claims, 4 Drawing Sheets

(56) References Cited

OTHER PUBLICATIONS

Iniesta, J., "Electrochemical oxidation of 3-methylpyridine at a boron-doped diamond electrode: application to electroorganic synthesis and wastewater treatment", Electrochemistry Communications, vol. 3, No. 7, pp. 346-351 (Jul. 1, 2001).

Mahe, E., "Electrochemical reactivity at graphitic micro-domains on polycrystalline boron doped diamond thin-films electrodes", Electrochimica Acta, Elsevier Science Publishers, Barking, GB, vol. 50, No. 11, pp. 2263-2277 (Apr. 1, 2005).

Panizza, M., "Application of diamond electrodes to electrochemical processes", Electrochimica Acta, Elsevier Science Publishers, Barking, GB, vol. 51, No. 2, pp. 191-199 (Oct. 10, 2005).

Rao, Tata N., "Electrochemical detection of carbamate pesticides at conductive diamond electrodes", Analytical Chemistry, American Chemical Society, US, vol. 74, No. 7, pp. 1578-1583 (Apr. 1, 2002).

Swain, G. M., "Solid Electrode Materials: Pretreatment and Activation", Handbook of Electrochemistry, Elsevier, NL, pp. 111-153 (Jan. 1, 2007).

Wang, J., "In situ electrochemical renewal of glassy carbon electrodes" Analytical Chemistry, vol. 60, No. 5, pp. 499-502 (Mar. 1, 1988).

International Search Report, PCT/EP2012/052689, dated Jan. 10, 2013.

Kraft, A., "Doped Diamond: A Compact Review on a New, Versatile Electrode Material," International Journal of Electrochemical Science, 2007, pp. 355-385.

Salazar-Banda, G.R., et al., "On the changing electrochemical behaviour of boron-doped diamond surfaces with time after cathodic pre-tratments," Electrochimica Acta 51, 2007, pp. 4612-4619, Elsevier Ltd.

Yagi, I, et al., "Electrochemical selectivity for redox systems at oxygen-terminated diamond electrodes," Journal of Electroanalytical Chemistry 473, 1999, pp. 173-178, Elsevier Science S.A.

METHOD OF ACTIVATING A DOPED DIAMOND ELECTRODE

CROSS REFERENCE TO RELATED APPLICATIONS OR PRIORITY CLAIM

This application is a National Phase of PCT/EP2012/052689, filed Feb. 16, 2012, entitled, "METHOD FOR ACTIVATING A DOPED DIAMOND ELECTRODE", which claims the benefit of French Patent Application No. 11 51341, filed Feb. 18, 2011, the contents of which are incorporated herein by reference in their entirety.

TECHNICAL FIELD

This invention belongs to the field of doped diamond-based electrodes, and their preparation and activation.

More particularly, this invention relates to a method of treating a doped diamond-based electrode capable of producing an electrode with an electrochemical reactivity by electrochemical activation which is high and stable over time and its use, in other words preferably with an electron transfer rate constant ($k_0$) greater than or equal to $10^{-3}$ cm/s.

STATE OF PRIOR ART

Doped diamond-based electrodes, and particularly electrodes based on boron-doped diamond, have the main advantages of having a large potential window, being stable in aqueous and organic media, having low residual currents and high resistance to chemical and electrochemical corrosion.

Consequently, these electrodes are particularly suitable for detection or analysis purposes, but also when the electrodes are particularly conducting and have high electrochemical reactivity, for applications such as electrochemical synthesis, treatment of waste water by electrolysis or as bioelectronic sensors.

Furthermore, since diamond is a biologically inert material, diamond electrodes may be implanted in the human body.

The electrochemical reactivity of an electrode may be related to its electron transfer rate constant ($k_0$). The higher the value of this constant ($k_0$), the greater the reactivity of the electrode. In this respect, it is considered that an electrode has a satisfactory electrochemical reactivity when its electron transfer rate constant ($k_0$) is greater than or equal to $10^{-3}$ cm/s.

Typically, this electron transfer rate constant ($k_0$) is measured by electrochemical impedance spectroscopy (EIS) at the open circuit potential (OCP) in the presence of a fast redox couple.

The electron transfer resistance ($R_T$) of an electrode is measured by placing the electrode concerned in an electrically conducting aqueous solution (electrolyte), particularly including a known concentration of a fast redox couple, for example such as an equimolar mix of potassium ferrocyanide and potassium ferricyanide.

The electron transfer rate constant ($k_0$) can then be defined according to equation (1) below:

$$k_0 = \left(\frac{R \times T}{N \times F}\right) \times \frac{1}{S \times F \times R_T \times C_0} \quad (1)$$

where R is the universal perfect gas constant,
T is the absolute temperature of the electrolyte (in Kelvin),
S is the electrode surface area (in cm$^2$),
F is the Faraday constant (96 485 C·mol$^{-1}$),
$R_T$ is the transfer resistance of the electrode (in Ohms),
$C_0$ is the concentration of the redox couple (in mol·cm$^{-3}$) and
N is the number of moles of electrons exchanged per mole from one or the other of the elements forming the fast redox couple used.

Studies have shown that the doping rate and the nature of surface terminations of a doped diamond electrode have an influence on the electrochemical reactivity of this electrode.

This is why it appears that the oxidised surfaces of the diamond (O terminations) are stable and hydrophilic but have lower reactivity, while conversely hydrogenated surfaces of the diamond (H terminations) have a hydrophobic nature associated with high reactivity (see document [1] referenced at the end of the description).

It would also appear that doping of the diamond, in fact boron doping, has a stabilising effect on the H terminations of the diamond (document [2]).

Therefore, it appears that in order to obtain a diamond electrode with a high electrochemical reactivity (in other words with a constant ($k_0$) greater than or equal to $10^{-3}$ cm/s), this electrode would have to have a hydrogenated surface and that it would preferably be made of doped diamond.

Unfortunately, exposure to air for several days or a single use as a work electrode induces a large drop in this reactivity due to oxidation of the H terminations and/or the potential clogging of this electrode by contaminating substances.

Therefore, doped diamond requires a surface treatment so that its electrochemical reactivity is increased (in the case of an initially partially or totally oxidised surface) or restored (in the case of an initially hydrogenated surface that would have been progressively oxidised); it is then said that the surface of the electrode is activated or reactivated.

Different methods of activation or reactivation of a doped diamond electrode aimed at optimising or restoring the electrochemical properties of the doped diamond have already been proposed in prior art.

For example, G. Salazar-Banda et al. (document [2]) perform an anodic pre-treatment of the doped diamond electrode at a voltage of +3 V/SHE ("Standard Hydrogen Electrode") for 30 minutes or a cathodic pre-treatment at a voltage of −3 V/SHE for 3 minutes and 30 minutes in an aqueous solution of $H_2SO_4$ with a concentration 0.5 mol·L$^{-1}$, in order to restore the reactivity of the doped diamond electrode.

A. Kraft (document [3]) performs an electrochemical oxidation in order to convert the H terminations into O terminations; subsequently the oxidised surface can once again be hydrogenated by applying a cathodic treatment in an acid aqueous electrolyte.

These different treatments have the disadvantage that they require very long activation treatment times (at least 30 minutes).

J. de Sanoit and E. Vanhove (document [4]), recommend the application of an alternately cathodic and anodic polarisation potential with increasing amplitude until anodic and cathodic current densities of between 10 µA/cm$^2$ and 1 mA/cm$^2$ are obtained. Although this approach can give doped diamond-based electrodes with improved properties in terms of the load transfer rate ($k_0$ greater than or equal to $10^{-3}$ cm/s), the stability and the reproducibility of electrochemical properties, it has the main disadvantage that it is very time consuming. An electrochemical activation operation lasts between 10 minutes (in galvanodynamic mode) and 30 minutes (in potentiodynamic mode).

Therefore, the inventors attempted to create an electrochemical activation method for a doped diamond electrode to obtain an electrode with a satisfactory load transfer rate ($k_0$ greater than or equal to $10^{-3}$ cm/s), and stable and reproducible electrochemical properties, in a much shorter electrochemical activation time than is currently possible with known activation methods according to prior art.

Note that the value of $10^{-3}$ cm/s applies to a value measured by electrochemical impedance spectroscopy at the open circuit potential (OCP) in the presence of a fast Redox couple.

PRESENTATION OF THE INVENTION

This purpose is achieved using an electrochemical method of activating a doped diamond-based electrode, said method including bringing the electrode into contact with an aqueous solution containing an electrolyte that may or may not contain electroactive species and application of an electrical excitation to said electrode in the form of one or several electrical pulses, in which each pulse contributes to activation of the electrode for a time $t_a$ provided that:

1°) the absolute value of the amplitude of this pulse during this time ta exceeds a threshold amplitude with one of the following values:
  when the electrolyte does not contain any electroactive species:
  1 $\mu A \cdot cm^{-2}$ if the pulse is a cathodic current pulse;
  3 $mA \cdot cm^{-2}$ if the pulse is an anodic current pulse;
  200 mV if the pulse is a cathodic voltage pulse; and
  2 V if the pulse is an anodic voltage pulse;
  when the electrolyte contains electroactive species:
  400 $\mu A \cdot cm^{-2}$ if the pulse is a cathodic current pulse;
  2 V if the pulse is a cathodic voltage pulse; and 2°) the activation time $t_a$ expressed in seconds is less than or equal to 10 for each pulse, and satisfies one of the following formulas for each pulse:

$$t_a \geq \frac{1}{n_c \times |J_{cMax}| \times K_1}$$

for a cathodic current pulse;

$$t_a \geq \frac{1}{n_a \times |J_{aMax}| \times K_2}$$

for an anodic current pulse;

$$t_a \geq \frac{1}{n_c \times |V_{cMax}| \times K_3}$$

for a cathodic voltage pulse;

$$t_a \geq \frac{1}{n_a \times |V_{aMax}| \times K_3}$$

for an anodic voltage pulse;
in which:
  $n_c$ is the total number of cathodic pulses forming the electrical excitation;
  $n_a$ is the total number of anodic pulses forming the electrical excitation;
  $|J_{cMax}|$ is the maximum value expressed as an absolute value in amperes per $cm^2$, of the cathodic current among the $n_c$ pulses;
  $|J_{aMax}|$ is the maximum value expressed as an absolute value in amperes per $cm^2$, of the anodic current among the $n_a$ pulses;
  $|V_{cMax}|$ is the maximum value expressed as an absolute value in Volts, of the cathodic voltage among the $n_C$ pulses;
  $|V_{aMax}|$ is the maximum value expressed as an absolute value in Volts, of the anodic voltage among the $n_a$ pulses;
  $K_1 = 10^4 \, A^{-1} \cdot cm^2 \cdot s^{-1}$;
  $K_2 = 10^2 \, A^{-1} \cdot cm^2 \cdot s^{-1}$;
  $K_3 = 0.1 \, V^{-1} \cdot s^{-1}$;

and in which the electrical excitation is applied for a total time $t_{tot}$ according to the following formula:

$$t_{tot} = \sum_{j=1 \text{ à } n} (t_{aj} + t_{ij})$$

where n is the total number of pulses forming the electrical excitation with $n = n_c + n_a$ and $t_{aj}$ is the activation time $t_a$ during which the $j^{th}$ pulse is active, $t_{ij}$ is the time $t_i$ during which the $j^{th}$ pulse is inactive and the $t_{aj}/t_{ij}$ ratio is greater than $10^{-4}$.

Note that in theory, all that is necessary for a pulse to contribute to activation of the electrode, is that the absolute value of its amplitude should be greater than zero. In practice, the absolute value of the amplitude of the pulse must be greater than an activation threshold value that depends on the electrolyte used. Thus, if it is assumed that $t_d$ is the duration of a pulse (duration during the start of the pulse and its return to the base line), $t_a$ is the active duration corresponding to the sum of the durations (within the duration $t_d$) for which the absolute value of the amplitude of the pulse is greater than the threshold value and $t_i$ is the sum of the durations (within the duration $t_d$) for which the absolute value of the amplitude of the pulse is less than the threshold value, then $t_d = t_a + t_i$ and the ratio $t_a/t_i$ for each pulse must be greater than 0.0001. The absolute value of the activation threshold value is equal to:

1 $\mu A/cm^2$ for a cathodic current pulse ($J_c$) in an ionic aqueous electrolyte not containing any electroactive species;
  400 $\mu A/cm^2$ for a cathodic current pulse ($J_c$) in an ionic aqueous electrolyte containing at least one electroactive species;
  3 $mA/cm^2$ for a anodic current pulse ($J_a$) in an ionic aqueous electrolyte not containing any electroactive species;
  2 V for a anodic voltage pulse ($V_a$) in an ionic aqueous electrolyte not containing any electroactive species;
  200 mV for a cathodic voltage pulse ($V_c$) in an ionic aqueous electrolyte not containing any electroactive species;
  2 V for a cathodic voltage pulse ($V_c$) in an ionic aqueous electrolyte containing electroactive species.

Note that an electrode in an electrolyte comprising electroactive species cannot be activated using anodic current or voltage pulses.

In the above and in the following, the term "electroactive species" refers to a species that is subject to a change in the oxidation state during a load transfer step.

Unlike what is normally done in activation methods according to prior art, there is no current or potential scan at a given scan rate; nor is a given potential applied and held for a given duration. In the method according to the invention current or potential pulses are applied.

Typically, a pulse is a short term variation of a physical magnitude (voltage, current, etc.) with a return to the initial state. Within the scope of the invention, "pulse" refers to a short voltage or current variation for a total time less than or equal to 10 s, followed by a return to the initial state (usually with amplitude equal to zero) of the voltage or current value.

Similarly, within the scope of the invention, "amplitude" refers to the maximum value of the anodic or cathodic voltage (or current) reached during an anodic or cathodic voltage (or current) pulse relative to a base line, usually equal to zero.

Consequently, a positive pulse may be considered as being a wave for which the amplitude relative to the base line increases and returns to the base line after a duration $t_d$. A negative pulse may be considered as being a wave for which the amplitude reduces relative to the base line and returns to the base line after a duration $t_d$.

Within the scope of the invention, it is preferable to have one or several pulses with maximum current or voltage amplitudes and the shortest possible time in order to activate the electrode as quickly as possible. It is also preferable to have electrical pulses with a maximum amplitude in a minimum activation time $t_a$.

In fact, the duration of a pulse is related to its amplitude, the type of electrolyte used and also the total number of pulses. Thus, even better results can be obtained by increasing the amplitude of a pulse and reducing the duration of its activation time or increasing the number of pulses.

Similarly, the amplitude, duration and number of pulses to obtain optimum activation of an electrode can vary from one experiment to another depending on the electrolyte used. Thus, optimum values of these parameters to activate a diamond-doped electrode in urine are not necessarily the same as the optimum values for activation in LiClO$_4$. However, a good result will always be obtained using one or several pulses lasting 10 s or less.

Advantageously, the duration and amplitude of each electrical pulse and the number of pulses are chosen such that the total duration of the electrical excitation is less than or equal to one minute. Preferably, the total duration of the electrical excitation $t_{tot}$ is less than or equal to 30 seconds, preferably less than or equal to 20 seconds, and even more preferably less than or equal to 10 seconds.

Within the scope of the invention, it is possible to obtain activation of the electrode using pulses with an activation time $t_0$ less than or equal to 10 s, less than or equal to 1 second, less than or equal to 100 milliseconds or even less than or equal to 10 milliseconds.

Within the scope of the invention, each electrical pulse may have any possible shape (square, triangular, sinusoidal, saw tooth, steps, or a mix of these shapes).

Preferably, each pulse is ideally rectangular in shape, in other words with walls at 90° and peaks at 180°.

When there are several pulses, the pulses may or may not be periodic; there can be a mix of periodic pulses and non-periodic pulses. Pulses may have the same shape or they may have different shapes. Pulses may possibly have the same activation time. Finally, pulses are not necessarily identical, in other words they may have different durations, amplitudes and/or shapes.

Obviously, conditions on the activation time $t_a$ and on the threshold value of the amplitude depend both on the fact that the electrolyte does or does not contain electroactive species and the fact that pulses are anodic pulses or cathodic pulses. In this respect, when the electrical excitation is formed from a mix of cathodic and anodic pulses, the two cases must be considered separately to determine the threshold activation time $t_a$ for anodic pulses and the threshold activation time $t_a$ for cathodic pulses.

Preferably, the ratio $t_a/t_i$ is chosen to be greater than or equal to 1 for each pulse.

Preferably, there are between 10 and 50 pulses.

Preferably, the pulses are periodic.

Preferably, the maximum amplitude of cathodic current pulses is between 400 µA/cm$^2$ and 5 mA/cm$^2$.

Preferably, the maximum amplitude of cathodic voltage pulses is between 2 V and 5 V.

Examples of electrolytes containing one or several electroactive species may be chosen from among an electroactive ionic salt (for example such as LiCl, NaCl, KCl), urine, blood, wine, a cola flavoured drink or sea water.

In other words, the electrolyte may contain at least one electroactive species chosen non-limitatively from among acids such as HNO$_3$ and HCl or mixes of them, salts such as LiCl, KCl and NaCl or mixes of them, and a saline phosphate buffer. The electrolyte containing at least one electroactive species may also be a more complex medium such as wine, cola flavoured drink, biological fluids containing proteins, enzymes, various organic compounds, urine or even blood.

In general, electroactive species comprise all acids, bases and organic or mineral salts for which the constituents change their oxidation state in the potential domain used.

Preferably, the electrolyte used for the electrochemical activation does not contain any electroactive species.

Non-limitative examples of electrolytes that do not contain electroactive species (that we will also refer to below as non electroactive electrolyte) may be chosen from among LiClO$_4$, NaClO$_4$, KClO$_4$ or a mix of them, Li$_2$SO$_4$, Na$_2$SO$_4$, K$_2$SO$_4$ or a mix of them. The non electroactive electrolyte may also for example be an acid such as H$_3$PO$_4$, HClO$_4$, H$_2$SO$_4$, an organic acid or mixes of them, a base such as LiOH, KOH, NaOH or mixes of them.

In general, non electroactive species comprise all acids, bases and organic or mineral salts for which the constituents do not change their oxidation state in the potential range used.

Preferably, the activation time $t_a$ of a pulse is about 100 milliseconds.

When the electrical excitation is in the form of several electrical pulses, the pulses may be pulses with negative amplitude values and pulses with positive amplitude values, possibly arranged alternately. Preferably, when the electrical excitation is in the form of several electrical pulses, at least one of the pulses is an anodic pulse and at least one the pulses is a cathodic pulse. According to one possible variant of the method, it is then preferable that the anodic pulse(s) should be alternated with the cathodic pulse(s).

Preferably, the doped diamond of the electrode is doped by a doping agent chosen from among the group composed of boron, nitrogen, phosphorus, nickel, sulphur and mixes of them.

One of the advantages of the method according to the invention is that it can be used to electrochemically activate an electrode based on doped diamond. It can also electrochemically reactivate such an electrode (in other words it can restore the initial reactivity of the electrode) that has lost all or some of its reactivity due to intensive use in the electrochemical measurement field (electrode, sensor, etc.).

Similarly, when the electrode has not been used for a long period of time, it is easy to perform the activation method according to the invention to activate the electrode before using it to make measurements, and thus to obtain reliable and reproducible results.

Consequently, this invention also relates to use of an electrochemical activation method as defined above to restore the electrochemical reactivity of a doped diamond-based electrode. In particular, it may be necessary to restore the electrochemical reactivity of a doped diamond-based electrode that has lost part of its reactivity following long term storage in air, subsequent to intensive analytic use in the electrochemical domain or after clogging by various organic compounds (biofilm, lipofilm, bacteria, microalgae, etc.).

Another advantage of the invention is that the aqueous solution containing an electrolyte that is used to activate the electrode and/or to restore the electrochemical reactivity of said electrode may possibly be the same aqueous solution in which the electrode loses its electrochemical reactivity. Thus, doped diamond electrodes that have lost their reactivity ($k_0$) due to their clogging in a medium (urine, blood, sea water, cola flavoured drink, etc.) may be reactivated within this medium using the activation method according to the invention.

A doped diamond-based electrode activated or reactivated using the method according to the invention may be used for the electrochemical analysis, detection of trace elements, etc., or as an electrode in biotechnology detectors and/or in grafting applications.

Such an electrode may also be used for depollution of effluents from chemical, metallurgical, food processing industries or from urban waste water.

Another advantage of the method according to the invention is that a doped diamond-based electrode can be activated or reactivated very quickly. By adapting the current or voltage density parameter, pulse duration parameter and the total duration of the electrical excitation parameter, the number of pulses, the concentration and the type of electrolyte, an electrode can quickly be obtained with an electron transfer rate constant ($k_0$) (measured by EIS at the open circuit potential with fast redox couple) greater than or equal to $10^{-3}$ cm/s.

For example, when current pulses are applied to the electrode, the time necessary to activate or reactivate the electrode reduces as the current applied during the activation increases.

Thus, unlike other known activation techniques that are relatively long, the activation method according to the invention may be done very quickly, in other words in less than 1 minute.

Furthermore, since the duration of the pulses is very short, the voltages or currents that have to be applied to activate an electrode according to the invention may have relatively high values that would degrade or destroy the electrode if an activation method according to prior art were used.

Furthermore, since the electrode may be activated within a wide range of ionic aqueous and pH solutions, including biological fluids (for example such as urine, blood, etc.) and environmental fluids (for example such as sea water, river water, etc.), the activation method according to the invention may be used in the biotechnology field and in the environmental field.

Finally, the electrochemical activation method according to the invention can considerably extend the working life of doped diamond electrodes while using minimum resources in a minimum time. Unlike surface treatment techniques described in prior art, for example anodic, cathodic and heat treatments, the activation method according to the invention is relatively easy to implement, it is fast and requires few resources (in many cases the electrolyte used may be simply the liquid medium in which the electrode lost its reactivity).

The invention will be better understood and other advantages and features will become clear after reading the following description given as a non-limitative example accompanied by the appended FIGS. 1 to 9.

DETAILED PRESENTATION OF PARTICULAR EMBODIMENTS

In this invention, the working electrode is a doped diamond-based electrode.

In the context of this invention, "doped diamond-based electrode" means any electrode for which doped diamond is the constituent or one of the constituents, doped diamond being any polycrystalline form of doped diamond with grain sizes varying from 5 nm to several micrometers (the grain size referring to the largest dimension of these grains).

Therefore, it is possible to have "ultrananocrystalline", "nanocrystalline" or "microcrystalline" diamond, depending on the grain size. Similarly, within the scope of this invention, a doped diamond-based electrode may equally well be an electrode composed solely of doped diamond, or an electrode in which the doped diamond only forms part of the electrode. In the latter case, the doped diamond may be in the form of a thin continuous or discontinuous layer, such as a surface film on a substrate.

The formation of a doped diamond-based electrode is known to those skilled in the art.

Growth of the doped synthetic diamond is usually obtained by making a thin doped diamond film grow on a substrate by plasma assisted chemical vapour deposition (CVD), the plasma possibly being created using an energy source such as microwaves (MPCVD deposit), Radio-Frequencies (RFCVD deposit) or a hot filament (HFCVD deposit). The result obtained is a doped diamond film with a thickness typically between 50 nm and 100 micrometers.

The chemical vapour deposition used comprises hydrogen and a carbon source, for example an alcane, usually methane, and a doping agent, for example boron. Within the scope of the invention, when the diamond is doped with boron, the boron concentration will preferably be between $10^{20}$ and $2 \times 10^{21}$ boron atoms per $cm^3$.

The device that we use to implement the activation method according to this invention is preferably a so-called three-electrode setup, in other words activation experiments are carried out in an electrochemical cell equipped with a reference electrode, a working electrode and a counter electrode.

Any reference electrode may be used. The reference electrode is either an SCE (Saturated Calomel Electrode), or an Ag/AgCl, [KCl]=3 M, reference electrode, or it may simply be a flame-cleaned platinum wire. In the latter case, it will be called a pseudo-reference electrode. In this respect, note that those skilled in the art are familiar with reference electrodes and know how to determine which reference electrode should be used, without any inventiveness.

The working electrode is the doped diamond electrode and the counter electrode may be a platinum grid with an area equal to at least five times more than the area of the working electrode.

Figure 2:
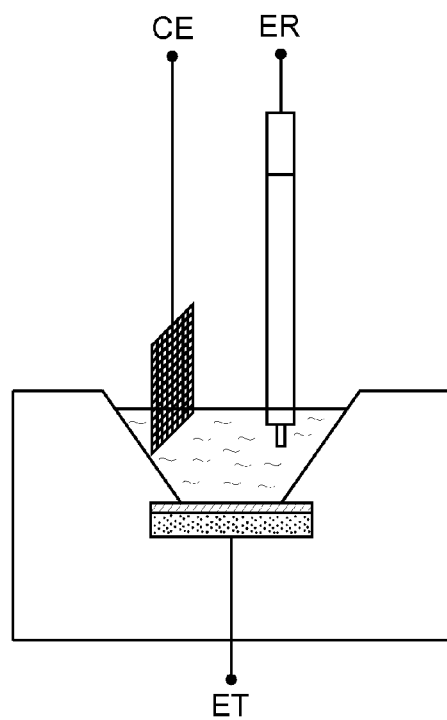
FIG. 2 diagrammatically shows the 3-electrode setup used to perform the electrochemical activation method according to the invention.

FIG. 2 shows an example of a possible three-electrode setup in which the counter electrode (CE) and the reference electrode (RE) are so-called immersed electrodes, while the working electrode (WE) forms the bottom of the electrochemical cell.

One variant of this setup is a setup with three immersed electrodes.

In some cases, it is also possible to not use a reference electrode; in this case, the standard two-electrode setup is used.

The electrolyte used in the electrochemical cell is an aqueous solution containing a non-electroactive electrolyte that is electrically conducting, for example such as $NaClO_4$, $KClO_4$ with any pH, or any NaOH. For illustration, the appropriate electrolyte for activation of a boron-doped diamond electrode may for example be $LiClO_4$ at a concentration of 0.5 M, without any prior adjustment of the pH value.

The activation method according to this invention consists of applying an electrical excitation in the form of one or several successive short term electrical pulses to the working electrode (doped diamond-based electrode) in contact with a particular electrolyte, each electrical pulse respecting two combined conditions, namely an activation time $t_a$ shorter than or equal to 10 seconds and longer than a threshold value time that depends on the electrolyte and on the fact that the pulse is an anodic or cathodic current/voltage pulse, and an amplitude greater than a threshold value amplitude.

For example, the activation of a doped diamond electrode in an $LiClO_4$ electrolyte is considered using a sequence of pulses containing cathodic current pulses only.

By applying the above two conditions, it is found that if pulses are to contribute to activation of the electrode, their current density must be more than 1 $\mu A/cm^2$ and their activation time must be longer than or equal to $1/(n \times J_c \times 10^4)$. Note that if a pulse does not satisfy the two conditions mentioned above, it is still included in the sequence of pulses but it does not contribute to activation and is therefore not counted in the total number of pulses n.

If a single cathodic current pulse of 10 $\mu A/cm^2$ is applied, then the activation time of this pulse must be at least $1/(1\times 10^{-5} \times 10^4)$, in other words 10 seconds. Since $t_a$ must also be less than or equal to 10 seconds, the activation time of the single cathodic current pulse will be equal to 10 seconds.

If ten 1 $\mu A/cm^2$ pulses are applied, then the activation time of each pulse is at least 10 seconds. Since $t_0$ must also be shorter than or equal to 10 seconds, each of the ten pulses will have an activation time of 10 seconds. If it is assumed that the time t, during which the pulses are inactive is 1 second, then the total electrical excitation time $t_{tot}$ composed of ten pulses is equal to 10×(10+1), namely 110 seconds.

If a single 100 $mA/cm^2$ pulse is applied, then the activation time of this pulse must be at least $1/(1 \times 10^2 . 10^{-3} \times 10^4)$, in other words 1 millisecond, and less than or equal to 10 seconds.

If we now consider the activation of a doped diamond electrode in an $LiClO_4$ electrolyte using a sequence of pulses containing only anodic current pulses, the pulses must have a current density exceeding 3 $mA/cm^2$ and an activation time equal to or exceeding $1/(n \times J_a \times 10^2)$ and less than or equal to 10 s.

If a single 10 $mA/cm^2$ pulse is applied, then the activation time of this pulse must be at least $1/(1 \times 10^{-2} \times 10^2)$, in other words 1 second.

If 100 100 $mA/cm^2$ pulses are applied, then the activation time of each pulse must be at least $1/(100 \times 10^{-1} \times 10^2)$, namely 1 millisecond.

If the activation of a doped diamond electrode is considered in an $LiClO_4$ electrolyte using a sequence of pulses containing only anodic voltage pulses, the voltage of the pulses must be more than 2 V and their activation time must be longer than or equal to $1/(n \times V_a \times 10^{-1})$ and less than or equal to 10 s.

If a single 5 V pulse is applied, the activation time of this pulse must be at least $1/(1 \times 5 \times 10^{-1})$ in other words 2 seconds.

The electrolyte may be other than $LiClO_4$, for example it may be urine. Thus, if the activation time of a doped diamond electrode in urine is considered using a sequence of pulses containing only cathodic current pulses, the current density of the pulses must be greater than 400 $\mu A/cm^2$ and their activation time must be longer than or equal to $1/(n \times J_c \times 10^4)$.

If 1000 500 $\mu A/cm^2$ pulses are applied, then the activation time of each pulse must be at least $1/(10^3 \times 500 \times 10^{-6} \times 10^4)$, namely 0.2 milliseconds.

If we now consider the activation of a doped diamond electrode in an $LiClO_4$ electrolyte using a sequence of pulses including cathodic current pulses and anodic current pulses, then the pulses that contribute to activation of the electrode are those among the anodic current pulses that have a current density greater than 3 $mA/cm^2$ and an activation time longer than or equal to $1/(n \times J_a \times 10^2)$ and those among the cathodic current pulses that have a current density exceeding 1 $\mu A/cm^2$ and an activation time longer than or equal to $1/(n \times J_c \times 10^4)$. Cathodic and anodic current pulses are dealt with separately.

Figure 1:
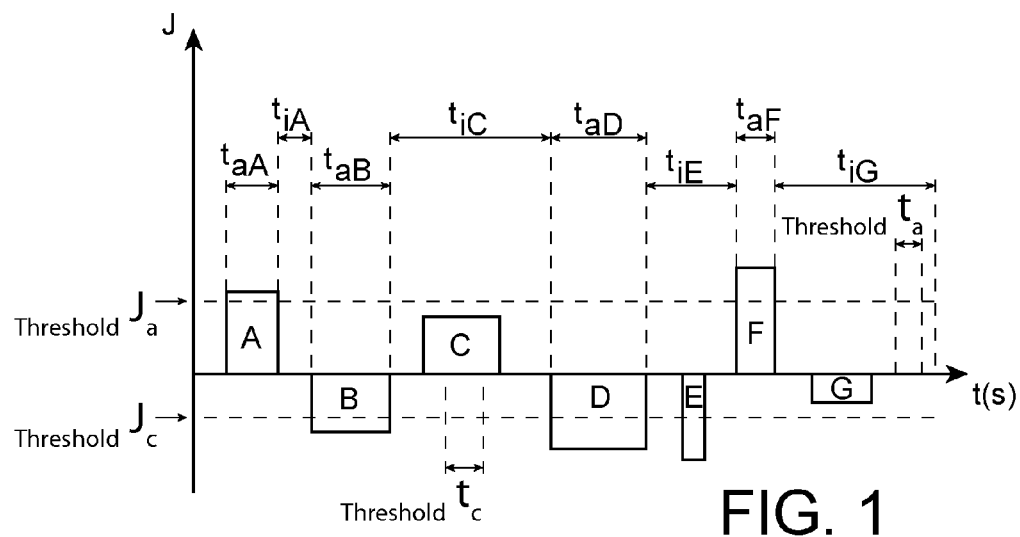
FIG. 1 shows an example of a sequence of anodic and cathodic current pulses, only some of which participate in electrochemical activation of a diamond electrode according to the method disclosed in the invention. Note that the dimensions are not shown to scale.

If we consider the example of the sequence of pulses shown in FIG. 1, it can be seen that some pulses do not satisfy the two conditions described above and therefore do not contribute to activation of the electrode.

Thus, of the three anodic current pulses, pulse "C" is not helpful because its maximum amplitude is below the threshold value. Pulses "A" and "F" are compared to calculate the minimum value for the activation time $t_a$: the maximum amplitude is the amplitude of pulse "F" and therefore this is the value used to calculate the minimum value of the activation time for anodic current pulses.

Similarly, pulses "E" and "G" among the cathodic current pulses are not suitable because the amplitude of one is below the threshold value and the activation time of the other is below the minimum value $t_a$. Thus, among the remaining pulses, the amplitude of pulse "D" is the highest and is used to calculate the value of the minimum activation time $t_a$.

Times $t_a$ and $t_i$ of each of the selected pulses are shown in FIG. 1. Therefore the total time of the electrical excitation is:

$$t_{tot} = \sum_{j=1 \text{ à } n} (t_{aj} + t_{ij})$$

where n=4 in other words $t_{tot} = t_{aA} + t_{iA} + t_{aB} + t_{iB} + t_{aD} + t_{iD} + t_{aF} + t_{iF}$ In fact, all sorts of combinations are possible between values of the number of pulses, their duration and amplitudes.

The range of available amplitude values is very wide. The choice of the value of the amplitude for a fixed duration and number of pulses is limited only by the capacity of the electrode to resist these pulses without being destroyed. By using short pulses, it is quite possible to apply pulses with large amplitude values to the electrode which will have the effect to very quickly leading to activation of the electrode without any risk of destroying the electrode.

Furthermore, for a given value of the pulse amplitude, better results can be obtained by increasing the duration of pulses and/or the number of pulses.

Therefore, the pulse amplitude may be chosen within a wide range of values.

For example, the voltage amplitude applied to the working electrode may be between 200 mV and 30 V.

The current pulse amplitude may for example be chosen within a range varying from 10 $\mu A/cm^2$ to 50 $mA/cm^2$.

The current pulse amplitude may also be equal to 0.5 $A/cm^2$, provided that the pulse duration is less than a few milliseconds, in other words less than 10 milliseconds.

A few examples of performances obtained for electrodes activated using the method according to the invention are given below.

A-1. Electrode #1 (Electrode B230210-7)

Electrode #1 is obtained by growing a thin film of boron-doped diamond by MPECVD (Microwave Plasma Enhanced Chemical Vapour Deposition) on a face of a 500 $\mu m$ thick boron-doped silicon substrate (111).

The electrode #1 obtained has a thin boron-doped diamond layer with a thickness of about 400 nm and a boron doping rate of more than $10^{20}$ and less than $2 \times 10^{21}$ atoms per $cm^3$.

The setup used is the 3-electrode setup shown in FIG. 2, in which the working electrode is electrode #1 and the boron-doped diamond surface area of electrode #1 in contact with the electrolyte is 0.33 $cm^2$.

A layer of Indium-Gallium eutectic alloy is placed between the silicon substrate of electrode #1 and a copper plate in order to create a resistive electrical contact (not shown).

The reference electrode is an Ag/AgCl, [KCl]=3 M type electrode, and the counter electrode is a platinum grid with an area of 4 $cm^2$.

The electron transfer rate constant ($k_0$) of electrode #1 is determined experimentally by performing electrochemical impedance spectroscopy (EIS) using an equimolar solution of a fast redox couple ($Fe(CN)_6^{3-/4-}$) at the equilibrium potential ($E_0$=+0.21 V/SCE). This is done using a 3-electrode setup like that shown in FIG. 2, electrode #1 forming the working electrode, a platinum wire acting as the reference electrode and a platinum grid forming the counter electrode, and keeping electrode #1 at an open circuit potential in a solution of 0.5 M of KCl containing an equimolar concentration at $10^{-3}$ M of a fast redox couple ($Fe(CN)_6^{3-/4-}$).

The EIS spectroscopy is done on a wide frequency range varying from 50 kHz to 10 Hz, with points spaced logarithmically and a voltage amplitude of 0.01 V rms.

For the non-activated electrode #1, a constant ($k_0$) equal to about $1.6 \times 10^{-3}$ cm/s is obtained.

After determining the value of the constant ($k_0$), electrode #1 is washed and then dried under an argon flow before cyclic voltammetry is applied to it in a 0.5 M KCl solution containing a $10^{-3}$ M concentration of a fast redox couple ($Fe(CN)_6^{3-/4-}$), which can give the amplitude of oxidation and reduction peaks (current and potential density) of electrode #1.

For a scanning rate of 0.1 V/s, the potential difference ($\Delta E_p$) between the oxidation and reduction peaks is measured at about 232 mV.

The anodic current density ($J_a$) is 182 $\mu A/cm^2$ and the cathodic current density ($J_c$) is equal to −191 $\mu A/cm^2$.

After obtaining all these measurements, electrochemical activation according to the invention is done on electrode #1.

This is done using the same 3-electrode setup as that used and described above to measure the constant ($k_0$), but the electrolyte is a 0.5 M solution of $LiClO_4$.

Since the electrode is electrochemically activated in an electrolyte not containing any electroactive species, it is possible to apply either a sequence of cathodic current, anodic current, cathodic voltage or anodic current pulses or a mix of several of these pulses, the pulses being required to satisfy the two conditions mentioned above, namely the condition on the minimum amplitude and the condition on the minimum activation time (where $t_a$ is less than or equal to 10 seconds).

If a sequence of cathodic current pulses is applied in such an electrolyte, the minimum value of the amplitude is −1 $\mu A/cm^2$. Thus, if it is required to apply 50 cathodic current pulses each with an amplitude of −1.5 $mA/cm^2$, then the minimum value of the activation time is $1/(50 \times 1,5.10^{-3} \times 10^4)$, namely 1.33 milliseconds.

Therefore, for example, it would be possible to choose an activation time $t_a$ equal to 0.1 s and an non-activation time $t_i$ (equal to the duration between two consecutive active pulses) also equal to 0.1 s, the duration of one pulse then being 0.2 s. The total activation time is (50×0.2), namely 10 s.

It can be seen that the ratio $t_a/t_i$ is much greater than $10^{-4}$.

The constant ($k_0$) measured after activation is about 0.04 cm/s and the potential difference between oxidation and reduction peaks is about 71 mV.

The anodic current density ($J_a$) is increased to 297 $\mu A/cm^2$ and the cathodic current density ($J_c$) is −306 $\mu A/cm^2$.

The results obtained before and after activation are given in table 1 below:

TABLE 1

|  | $k_0$ (cm/s) | $\Delta E_p$ (mV) | $J_a$ ($\mu A/cm^2$) | $J_c$ ($\mu A/cm^2$) |
|---|---|---|---|---|
| Before activation | ≈0.0016 | ≈232 | 182 | −191 |
| After activation | ≈0.04 | ≈71 | 297 | −305 |

Figure 3:
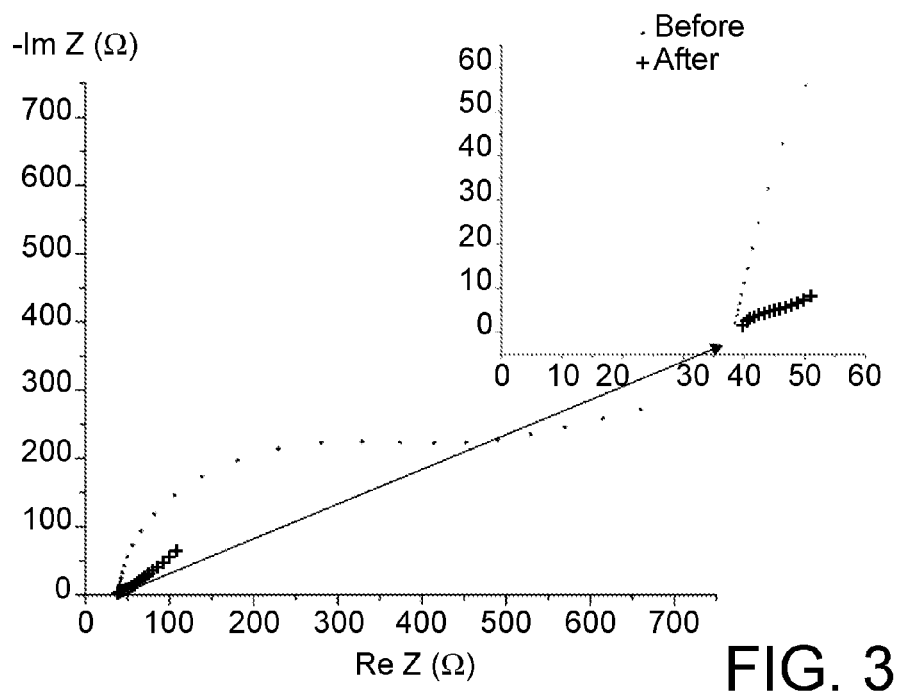
FIG. 3 shows two electrochemical impedance spectroscopies (EIS) of electrode #1, before and after electrochemical activation respectively, using the method according to the invention, a magnification of a portion of these two spectra being added in the upper part of FIG. 3.
Figure 4:
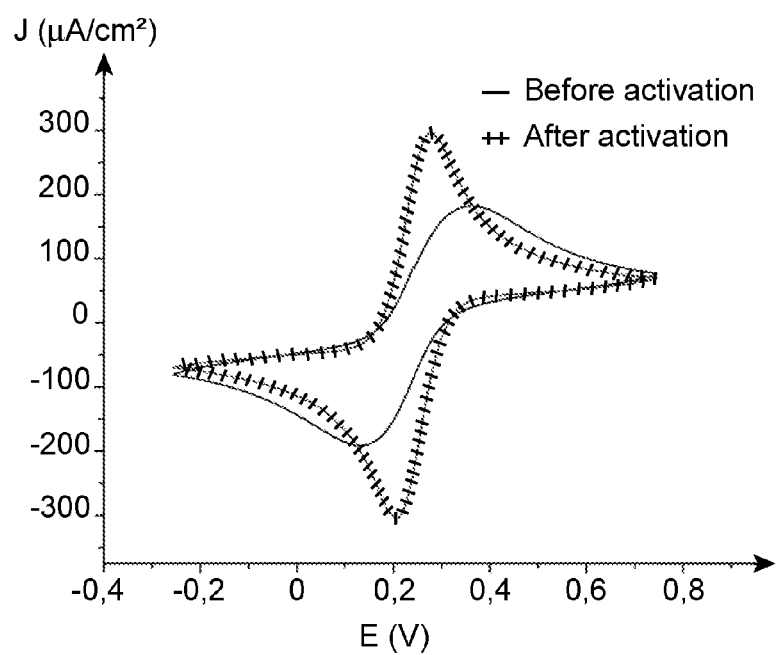
FIG. 4 shows the cyclic voltammetry of electrode #1 as defined below, before and after its activation using the electrochemical activation method according to the invention.

FIGS. 3 and 4 show the results obtained before and after activation of electrode #1 for electrochemical impedance spectroscopies (EIS) (FIG. 3) and for cyclic voltammetries (FIG. 4) respectively.

It is found that before activation, the initial reactivity of electrode #1 is satisfactory ($k_0$≈0.0016 cm/s) while the cyclic voltammetry curves (corrected for the resistive drop) show a significantly greater difference between the anodic and cathodic peaks ($\Box E_p$) than the theoretical value of 60 mV.

Activation according to the invention can increase the value of ($k_0$) (and therefore the reactivity of the electrode) by a factor of 25 and reduce the potential difference between oxidation and reduction peaks by a factor of 3, by applying an electrical excitation in the form of 50 pulses for a total duration ($t_{tot}$) of only 10 seconds.

Figure 5:
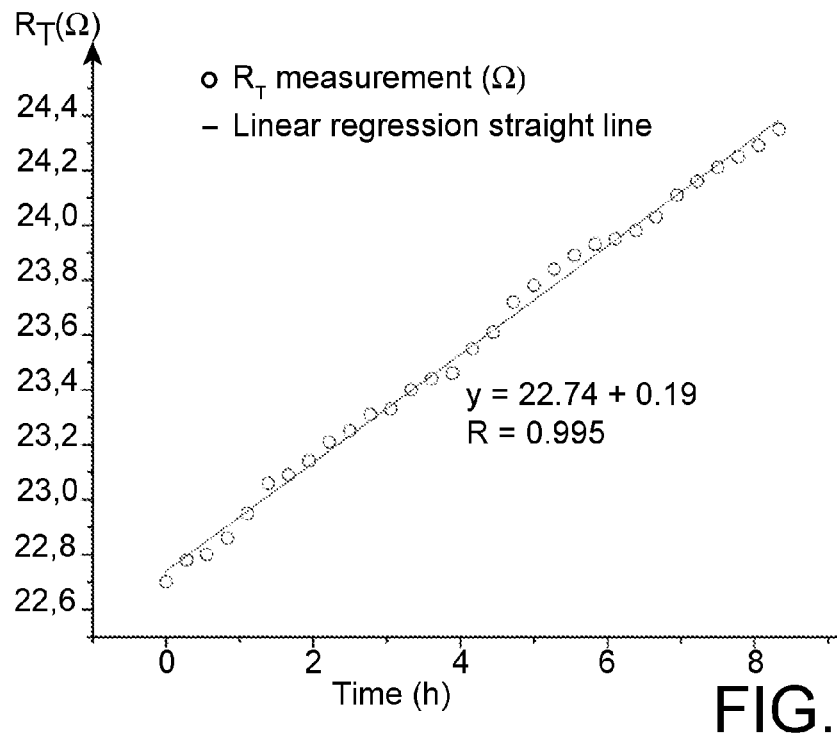
FIG. 5 shows the stability of the transfer resistance $R_T$ of the electrode #1 activated using the activation method according to the invention, over time.

Furthermore, the reactivity of electrode #1 thus activated is stable in time, as can be seen with reference to FIG. 5, showing stability of the transfer resistance $R_T$ of the activated electrode #1, over time.

A-2. Electrode #2 (Electrode B71209-16)

Like electrode #1 above, electrode #2 is obtained by growing a thin film of boron-doped diamond by MPCVD deposition on a face of a 500 μm thick boron-doped silicon substrate (111), thus obtaining a thin boron-doped diamond layer with a thickness of about 400 nm and a boron concentration of more than $10^{20}$ atoms per $cm^3$.

A cyclic voltammetry with a scanning rate of 0.1 V/s during three scans was made in human urine (FIG. 6), using electrode #2 as the working electrode, a platinum grid with an area of 4 $cm^2$ as a counter electrode and an Ag/AgCl, [KCl]=3 M electrode as the reference electrode in a 3-electrode setup.

Figure 6:
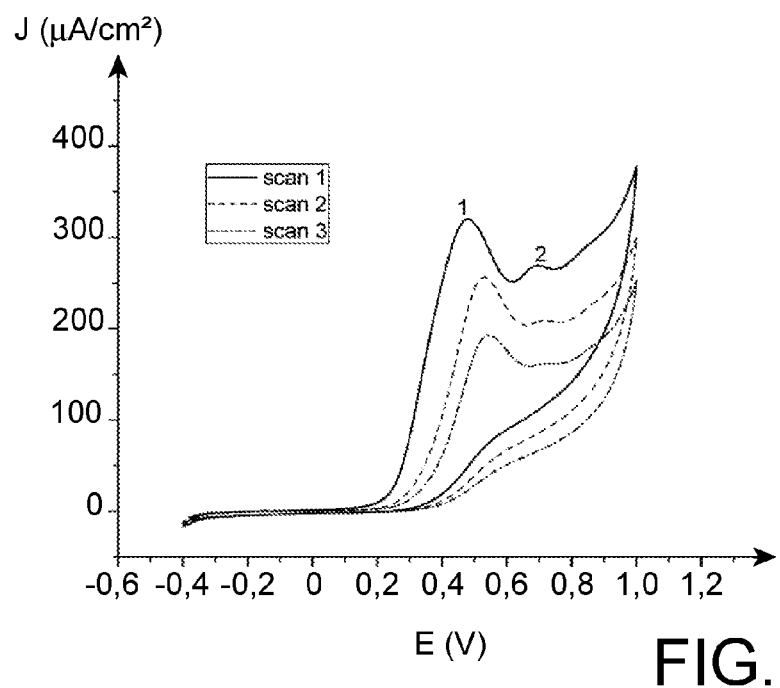
FIG. 6 shows the cyclic voltammetry of the non-activated electrode #1, made in urine, during three successive scans, showing degradation of the electrochemical capacities of the non-activated electrode #1 as the different scans are made.

In FIG. 6, two oxidation peaks (1) and (2) can be detected from cyclic voltammetry curves, these peaks corresponding to oxidation potentials of 0.3-0.55 V and 0.6-0.7 V respectively. It can be seen that the amplitude of these three peaks reduces as successive scans are made, due to clogging of the working electrode. It can also be seen that the oxidation peaks (1) and (2) are shifted towards higher potential values as successive scans are made. Clogging of the electrode may be related to the loss of reactivity of the electrode, in other words loss of the capability to exchange electrons with electrochemically active species quickly.

Figure 7:
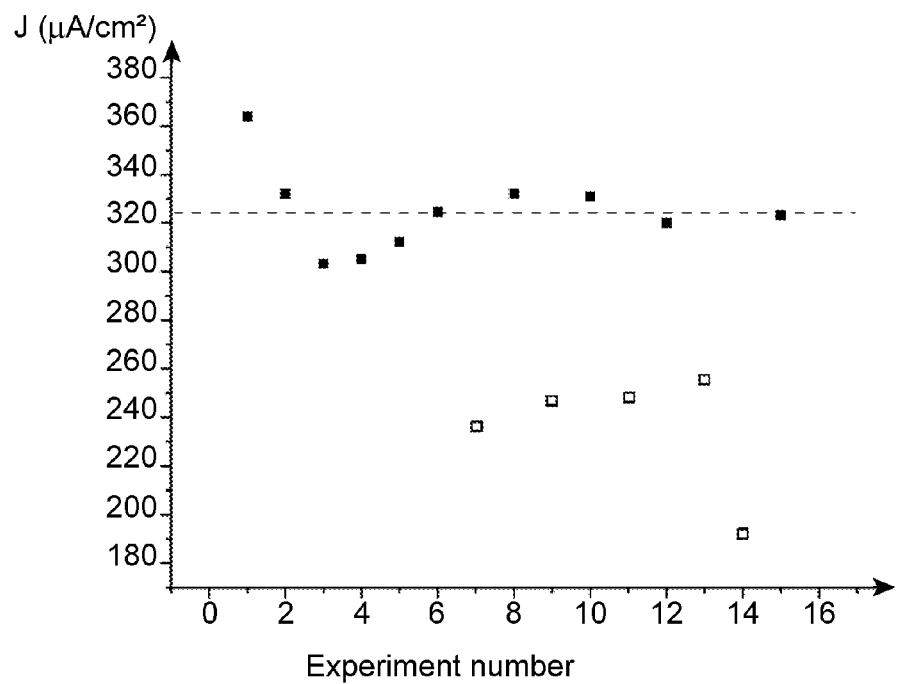
FIG. 7 shows the value of the current density of the first peak obtained during the first cyclic voltammetry scan for different tests made with electrode #2.
Figure 8:
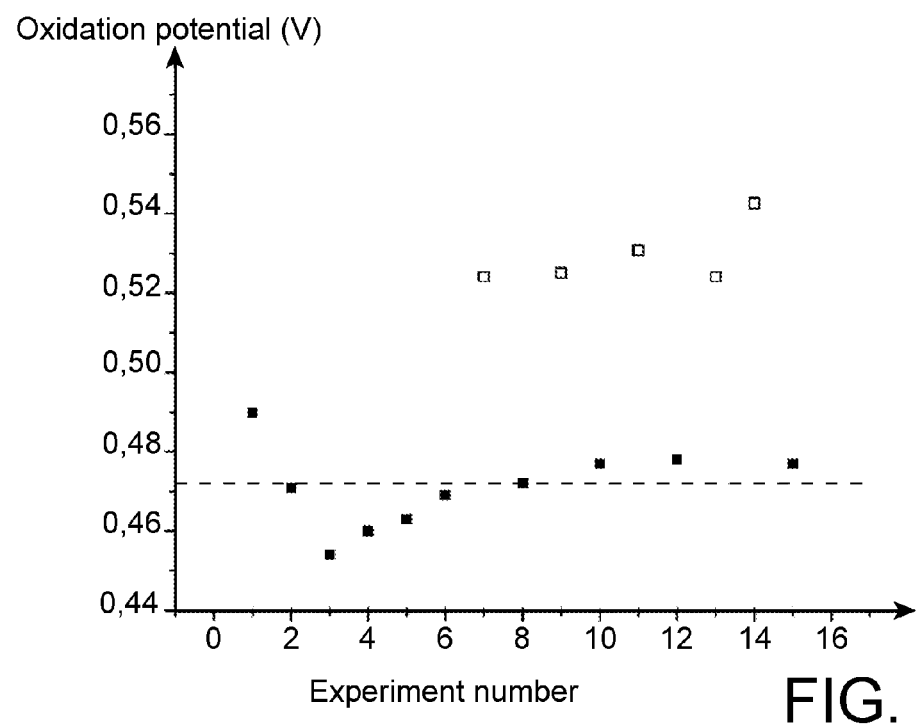
FIG. 8 shows the value of the oxidation potential of the first peak obtained during the first cyclic voltammetry scan for different tests made with electrode #2.

A sequence of 15 cyclic voltammetry experiments each comprising two scans, was done in human urine; the current density and the absolute value of the oxidation potential of the first peak of the first scan was recorded for 14 experiments and the absolute value of the oxidation potential of the first peak of the second scan was recorded for one of the experiments (corresponding to the electrode used during experiment number 14). The results obtained are shown in FIGS. 7 and 8 respectively.

Each electrode used is an electrode #2 like the one described above (measurement symbolised by a solid square) and each electrode except for the electrodes used in experiments numbers 7, 9, 11, 13 and 14 (measurement symbolised by a hollow square), has firstly been activated in urine.

In this case, since the electrolyte contains electroactive species, the electrochemical activation of the electrode can only be done by cathodic current pulses, cathodic voltage pulses or a mix of these pulses.

If it is decided to apply a sequence of cathodic current pulses in such an electrolyte, then the minimum value of the amplitude is −400 μA/$cm^2$. Thus, if it is required to apply 50 cathodic current pulses each with an amplitude of −15 mA/$cm^2$, then the minimum value of the activation time is $1/(50 \times 15 \cdot 10^{-3} \times 10^4)$, namely 0.133 milliseconds.

Therefore, an activation time $t_a$ and an inactivation time $t_i$ of 0.1 s can be chosen, corresponding to an electrical excitation formed from 50 pulses applied for a total duration of 10 seconds.

Comparing the results obtained during the 15 experiments (FIG. 7), it can be seen that the current density amplitude of the oxidation peak (1) is very much reduced when a cyclic voltammetry is done using a non-activated electrode #2, while the amplitude remains practically the same for activated electrodes (the mean current density obtained using the mean of the measurements obtained with the activated electrodes being 324 μA/$cm^2$ and being represented by the dashed line).

For experiment No. 14 which, as mentioned above, corresponds to the absolute value of the oxidation potential of the first peak of the second scan with a non-activated electrode #2, it can be seen that the absolute value of the peak is even lower than for the other experiments 7, 9, 11 and 13 made with non-activated electrodes.

Similarly, it can be seen in FIG. 8 that the value of the oxidation potential of electrodes 7, 9, 11, 13 and 14 that were not activated increases (increased anodic potential) relative to the mean oxidation potential (the average current density (obtained by taking the mean of measurements made with activated electrodes) being 0.472 V and being represented by the dashed line).

These two examples have just confirmed that the activation method according to the invention can give electrodes with high reactivity performances.

We will now describe a few example applications of the electrochemical activation method according to the invention.

B.1. Urine Analysis

Considering the cost effectiveness, the precision of measurements and the short time necessary for quantification of the analytes, electrochemical measurement techniques are more beneficial than other techniques.

Consequently, doped diamond-based electrodes and particularly boron-doped diamond-based electrodes, are frequently used as electrochemical sensors.

Furthermore, doped diamond-based electrodes and particularly boron-doped diamond-based electrodes, are robust and resistant to corrosion, which makes them particularly suitable for use as electrochemical sensors.

Doped diamond-based electrodes, and particularly boron-doped diamond-based electrodes, can thus be used as electrochemical sensors for analysis of a patient's urine and for the detection of many analytes. One or several analytes present in a patient's urine often have to be checked and quantified in real time, particularly for patients admitted into intensive care units.

As observed previously in FIG. 6, although a boron-doped diamond electrode can detect the two oxidation peaks of a cyclic voltammetry done in urine, the amplitude of these peaks tends to decrease as the successive scans continue, due to clogging of the working electrode.

It would be very expensive to replace the boron-doped diamond working electrode after each measurement and it would be difficult to perform electrode surface treatments, for example hydrogenation in a hydrogen plasma.

The activation method according to the invention can restore the reactivity of the working electrode by electrochemically activating it in an aqueous electrolyte in less than 10 seconds. It is quite possible to do the activation within the electrolyte in which the electrode became clogged, as described above with urine, and to restore almost the same reactivity as said activated electrode had before it became clogged.

B.2. Control of Environmental Pollutants

Environmental pollutants, for example such as trinitrotoluene (TNT) used as an explosive material, have undesirable effects such as carcinogenic effects, anaemia, hepatic reactions, mutagenic effects, on humans.

Doped diamond-based electrodes and particularly boron-doped diamond-based electrodes can be used for detection of TNT.

For example, traces of TNT have been recorded in different marine areas following leaks from sea mining operations and measured using BDD electrodes (document [5]). However, due to the presence of species with a high molecular mass, the electrodes quickly became clogged during a long measurement (in other words lasting several hours); use of the activation method according to the invention can quickly reactivate the electrodes and improve their reuse. Furthermore, with the method according to the invention, electrodes can be reactivated directly in the solution to be analysed, provided that this solution is an aqueous solution comprising an electrically conducting electrolyte.

BIBLIOGRAPHY

[1] I. Yagi et al
*Journal of Electroanalytical Chemistry*, (1999), 473, pp 173-178
[2] G. Salazar-Banda et al
"*On the changing electrochemical behaviour of boron-doped diamond surfaces with time after cathodic pre-treatments*", Electrochimica Acta 51 (2006), p 4612-4619
[3] A. Kraft
"*Doped Diamond: A Compact Review on a New, Versatile Electrode Material*", Int. J. Electrochem. Sci., 2 (2007), p 355-385
[4] J. de Sanoit and E. Vanhove
"Procédé d'activation d'une électrode to base de diainant, électrode ainsi obtenue et ses utilisations" (Method of activating a diamond-based electrode, electrode thus obtained and its uses), WO 2008/148861, 2008
[5] J. de Sanoit et al
"*Electrochemical diamond sensors for TNT detection in water*", Electrochimica Acta 54 (2009), p 5688-5693

The invention claimed is:

1. Electrochemical method of activating a doped diamond-based electrode, the method including bringing the electrode into contact with an aqueous solution containing an electrolyte that does not contain electroactive species and applying an electrical excitation to said electrode in the form of one or several electrical pulses, in which each pulse contributes to activation of the electrode for a time $t_a$ provided that:

1°) the absolute value of the amplitude of this pulse during this time $t_a$ exceeds a threshold amplitude with one of the following values:
1 µA·cm$^{-2}$ if the pulse is a cathodic current pulse;
3 mA·cm$^{-2}$ if the pulse is an anodic current pulse;
200 mV if the pulse is a cathodic voltage pulse; and
2 V if the pulse if an anodic voltage pulse; and 2°) the activation time $t_a$ expressed in seconds is less than or equal to 10 for each pulse, and satisfies one of the following formulas for each pulse:

$$t_a \geq \frac{1}{n_c \times |J_{cMax}| \times K_1}$$

for a cathodic current pulse;

$$t_a \geq \frac{1}{n_a \times |J_{aMax}| \times K_2}$$

for an anodic current pulse;

$$t_a \geq \frac{1}{n_c \times |V_{cMax}| \times K_3}$$

for a cathodic voltage pulse;

$$t_a \geq \frac{1}{n_a \times |V_{aMax}| \times K_3}$$

for an anodic voltage pulse;

in which:
$n_c$ is the total number of cathodic pulses forming the electrical excitation;
$n_a$ is the total number of anodic pulses forming the electrical excitation;
$|J_{cMax}|$ is the maximum value expressed as an absolute value in amperes per cm$^2$, of the cathodic current among the $n_c$ pulses;
$|J_{aMax}|$ is the maximum value expressed as an absolute value in amperes per cm$^2$, of the anodic current among the $n_c$ pulses;
$|V_{cMax}|$ is the maximum value expressed as an absolute value in Volts, of the cathodic voltage among the $n_c$ pulses;
$|V_{aMax}|$ is the maximum value expressed as an absolute value in Volts, of the anodic voltage among the $n_a$ pulses;
$K_1 = 10^4$ A$^{-1}$·cm$^2$·s$^{-1}$;
$K_2 = 10^2$ A$^{-1}$·cm$^2$·s$^{-1}$;
$K_3 = 0.1$ V$^{-1}$·s$^{-1}$;
and in which the electrical excitation is applied for a total time $t_{tot}$ according to the following formula:

$$t_{tot} = \sum_{j=1 \grave{a} n} (t_{aj} + t_{ij})$$

where n is the total number of pulses forming the electrical excitation with $n = n_c + n_a$ and $t_{aj}$ is the activation time $t_a$ during which the $j^{th}$ pulse is active, $t_{ij}$ is the time $t_i$ during which the $j^{th}$ pulse is inactive and the $t_{aj}/t_{ij}$ ratio is greater than $10^{-4}$.

2. Method according to claim 1, in which said electrical pulse(s) has(have) a maximum amplitude in a minimum activation time $t_a$.

3. Method according to claim 1, in which the ratio $t_a/t_i$ is greater than or equal to 1 for each pulse.

4. Method according to claim 1, in which there are between 10 and 50 pulses.

5. Method according to claim 1, in which the pulses are periodic.

6. Method according to claim 1, in which the maximum amplitude of the cathodic current pulses is between 400 µA/cm$^2$ and 5 mA/cm$^2$.

7. Method according to claim 1, in which the maximum amplitude of the cathodic voltage pulses is between 2 V and 5 V.

8. Method according to claim 1, in which the activation time $t_a$ of a pulse is about 100 milliseconds.

9. Method according to claim 1, in which, when the electrical excitation is in the form of several electrical pulses, at least one of the pulses is an anodic pulse and at least one of the pulses is a cathodic pulse.

10. Method according to claim 1, in which, when the electrical excitation is in the form of several electrical pulses, at least one of the pulses is an anodic pulse and at least one of the pulses is a cathodic pulse, and in which the anodic pulse(s) are alternated with the cathodic pulse(s).

11. Method according to claim 1, in which the electrolyte that does not contain any electroactive species is chosen from among LiClO$_4$, NaClO$_4$, KClO$_4$ or a mix of them, Li$_2$SO$_4$, du Na$_2$SO$_4$, K$_2$SO$_4$ or a mix of them.

12. A method according to claim 1, wherein the method is used to restore the electrochemical reactivity of a doped diamond-based electrode.

13. A method according to claim 1, wherein the method is used to restore the electrochemical reactivity of a doped diamond-based electrode, in which the aqueous solution containing an electrolyte used to restore the electrochemical reactivity of said electrode is the same aqueous solution in which the electrode lost its electrochemical reactivity.

* * * * *